United States Patent [19]
Hsia et al.

[11] 4,235,792
[45] Nov. 25, 1980

[54] IMMUNOLOGICAL MATERIALS

[75] Inventors: Jen C. Hsia; Chou-Tok Tan, both of Toronto, Canada

[73] Assignee: The Governing Council of the University of Toronto, Toronto, Canada

[21] Appl. No.: 787,524

[22] Filed: Apr. 14, 1977

[51] Int. Cl.$^3$ ............................ C07F 9/09; C07J 9/00
[52] U.S. Cl. ..................................... 260/403; 260/402; 260/941; 260/944; 260/397.2; 562/451; 424/319; 424/238; 424/260; 424/12; 546/66
[58] Field of Search ............ 260/941, 403, 402, 397.2, 260/944; 424/12; 562/451

[56] References Cited

U.S. PATENT DOCUMENTS

| 3,880,934 | 4/1975 | Rammler | 424/12 |
| 3,882,225 | 5/1975 | Patel et al. | 424/12 |
| 3,890,834 | 9/1975 | Goldstein et al. | 424/12 |
| 3,951,748 | 4/1976 | Devlin | 424/12 |

FOREIGN PATENT DOCUMENTS 1194256  6/1967  United Kingdom ...................... 424/12

Primary Examiner—Anton H. Sutto
Attorney, Agent, or Firm—Ridout & Maybee

[57] ABSTRACT

Immune lysis of sensitized liposomes containing a marker is employed in an assay method wherein an antigenic material to be determined is reacted with a specific antiserum and the degree of inhibition of the antiserum is detected by the extent of release of a marker when the antiserum reacts with liposomes containing a sensitizer specific to the antiserum.

5 Claims, No Drawings

IMMUNOLOGICAL MATERIALS

BACKGROUND OF THE INVENTION

1. Field of the Invention

The invention relates to immunological methods and materials and more especially to methods and materials for determining minute quantities of antigenic materials. The term "antigenic materials" as employed in this specification means substances having chemically-defined molecules with which an antibody can react, and includes antigens and haptens.

2. Description of the Prior Art

There are known immunological materials, usually called liposomes, which comprise a lipid bilayer structure and which can contain entrapped markers. Sensitized liposomes have been described by Kinsky and others in for example Biochemistry, Vol. II, No. 22, 1972, pp. 4085–4093.

These sensitized materials may be prepared in known manner from an aqueous mixture of a phospholipid e.g. lecithin and/or sphingomyelin, a sterol, e.g. chlosterol, a charged amphiphile e.g. dicetyl phosphate, together with a fourth component, known as a sensitizer, which serves to render the product sensitive to lysis by a specific antiserum in the presence of complement. The sensitizer molecule comprises an amphiphilic body portion having an apolar tail and a polar intermediate portion to which is joined an antigenic head.

In the preparation of the liposomes or other lipid bilayer structure, an aqueous solution containing the marker is introduced, and the aqueous marker solution becomes entrapped by the lipid layers within the structure of the product. The marker serves to indicate lysis, since the released marker can be detected, and the quantity of marker released can be determined.

One especially preferred form of marker is the spin label type of marker as described by McConnell et al in Proc. Nat. Acad. Sci. USA Vol. 71, No. 5, pp. 1691–1964, May 1974. These spin label markers permit the application of very convenient electron spin resonance (ESR) techniques for monitoring the lysis. Other detectable marker materials can however be employed e.g. glucose as proposed by Kinsky et al.

Before the present invention these reagents and techniques have been employed mainly for studying matters of scientific interest in connection with the structure of and the mechanism of lysis of lipid membranes.

SUMMARY OF THE INVENTION

It has been appreciated in this invention that these lipid bilayer structures may be applicable to the assay of aqueous specimens containing an unknown and minute content of antigenic material and investigation has shown that an assay procedure for determining minute quantities of antigenic material can be successfully conducted to a higher degree of accuracy using these structures.

In such assay, an aqueous antigenic material-containing specimen is reacted with an antiserum for the antigenic material, so that there is obtained an antiserum which has a level of antibody activity which is inhibited to a certain extent depending on the content of antigenic material originally present in the specimen. This reduced-activity antiserum is thereafter reacted in the presence of the usual complement with a lipid bilayer structure containing trapped marker, and it has been found that under standardized conditions, the amount of marker released is detectably related to the content of antigenic material in the original specimen through a predetermined, generally inverse, relationship. Thus, by employing standardized reagents, an assay can be conducted to reveal the content of antigenic material in a specimen of unknown, very small concentration.

As a result of development of a prior immunoassay method, namely radio immunoassay, there are commercially available a number of specific antisera for antigenic materials of interest, including antisera for materials towards which organisms, including the human body, do not normally exhibit an immune reaction. The present assay technique is, however, more convenient, and is at least as sensitive and may possess greater accuracy than the known radio immunoassay. Further, in accordance with the teachings of this invention, it is possible to prepare a wide range of synthetic sensitizers with varied and diverse antigenic heads covalently coupled to amphiphilic molecules and these different sensitizers can be employed to produce a range of sensitized liposome structures, whereby the assay technique is capable of application to the assay of a range of diverse substances, and especially to assay of antigenic materials of biological or physiological interest, preferably antigenic materials which are of interest in connection with the human biology and the human physiology.

As will be appreciated by those skilled in the art, there exists the possibility of employing a wide range of compounds as the amphiphilic portion of the sensitizer compound.

DESCRIPTION OF THE PREFERRED EMBODIMENTS

In the preferred form of the present invention, the sensitizer compound comprises an antigenic material of interest covalently coupled to an amphiphilic compound which has an intermediate polar portion joined to an aliphatic or alicyclic lipophilic group.

Examples of suitable amphiphilic compounds include phosphatidylethanolamine compounds of formula

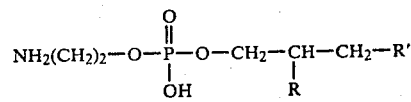

wherein R and R' can independently be H, OH, R", OR", or

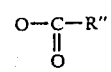

where R" is a saturated or unsaturated, branched or straight chain alkyl or alkylene group of 1 to 24 carbons, and wherein at least one of R and R' is

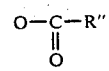

or —OR".

Other examples of amphiphilic molecules include fatty acids, cholesterols, sphingo-phospholipids, sphingosin of formula

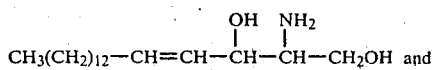

dihydro sphingosin of formula

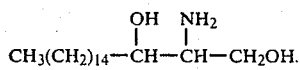

Described in more detail hereinafter is an example of the preparation of compounds containing an alicyclic steroid-type residue, namely the residue of 3β-hydroxycholestane of formula

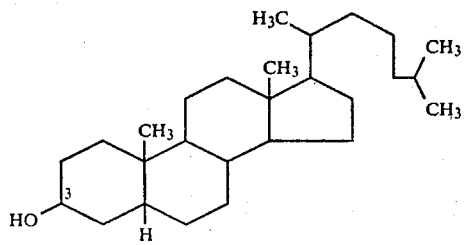

It has been established that with functionally effective sensitizers, the sensitizer compound is capable of forming together with the other components of the lipid bilayers a membrane-like bilayer in which the sensitizer forms an integral part of the membrane and in which the haptenic head of the sensitizer protrudes from the membrane into the surrounding aqueous phase so that it is available for binding with a specific antibody. Thus it is considered that the amphiphilic portion of the sensitizer compound is the portion which locates the haptenic head relative to the lipid bilayer.

In coupling the antigenic material of interest to the amphiphilic molecule, a variety of coupling reagents and coupling reactions may be employed. Thus, for example, a carboxylic acid group of an antigenic material may be coupled to an amino group of an amphiphilic molecule by direct reaction to produce an antigenic N-substituted amide wherein the N-substituent is the residue of the amphiphilic molecule. In other examples, a distinct reagent is employed to couple the antigenic material to the amphiphilic molecule and this coupling reagent may be reacted initially with either the antigenic material or with the amphiphilic molecule to produce a reactive intermediate or a sensitizer precursor which can thereafter be further reacted to produce the final sensitizer compound. Examples of such coupling reagents include acyl isocyanates, 4-fluoro-3-nitrophenyl azides, and maleic acid and derivatives, which may be reacted with available amine groups to obtain N, N'-substituted maleimides. One presently preferred coupling reagent is 1,5-dihalo-2,4-dinitrobenzene and in one procedure for coupling a hapten to the amphiphilic molecule, a 2,4-dinitro-5-halo-phenylated derivative of the amphiphilic compound is formed by reacting 1,5-dihalo-2,4-dinitro benzene with an amphiphilic compound or with a compound reactable with an amphiphilic compound and having a nucleophilic group e.g. amino, mercapto, or phenoxide anion, to form a sensitizer precursor. Such a sensitizer precursor will typically have a 2,4-dinitro-5-halo-phenyl group linked through a divalent polar residue to an aliphatic or alicyclic lipophilic group.

Further examples of coupling agents include 4,4'-dihalo-3,3' dinitrophenyl sulfones of formula

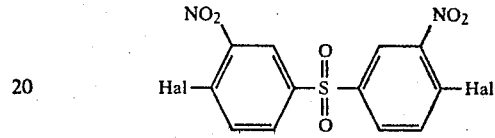

where Hal is halo group. Similarly to the dihalo-dinitrobenzene compounds mentioned above, these sulfones can be reacted with an amphiphilic compound having a nucleophilic group to form a sensitizer precursor having a halo group available for coupling with an antigenic material molecule having a nucleophilic group.

Examples of sensitizer precursors include the phenylated derivatives of phosphatidyl esters of hydroxy amines or of aminoacylated compounds wherein the hydroxy amine is acylated with an acyl group derived from an amino acid having one or more amino groups, such as the phenylated derivative of e.g. phosphatidylethanolamines of formula:

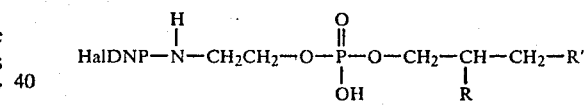

or of aminocaproyl phosphatidylethanolamines of formula:

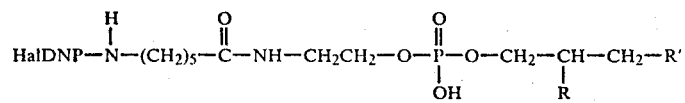

or of diamino carboxy compounds, e.g. of lysyl phosphatidylethanolamine of formula:

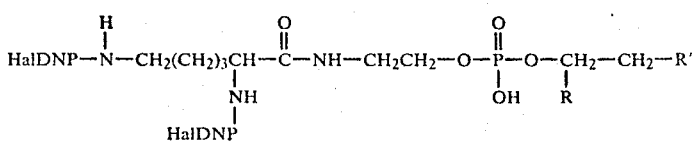

wherein HalDNP is 2,4-dinitro-5-halo-phenyl group, and R and R' are as defined before.

The N,N'-di-substituted lysyl compound referred to above is exemplary of a class of multivalent sensitizer precursors of especial interest. These precursors can be reacted with hapten to produce multivalent sensitizer molecules having two or more antigenic material residues on a single molecule. These antigenic material residues are separated in the molecule by distances of only a few bond lengths. When multivalent sensitizers are incorporated into a liposome it is found that the onset of complement-induced lysis may be more rapid than where a monovalent sensitizer is employed and the lysis may proceed more efficiently. The reason for this phenomenon is not completely understood, but it appears that lateral proximity of antibody-binding sites tends to induce a more rapid immune lysis.

The 5-halo group in the above-mentioned halo-dinitro-phenylated precursors is available for coupling with antigenic materials containing a nucleophilic group such as -amino, -mercapto, or phenoxide anion with which the precursor can combine through nucleophilic substitution on the benzene ring.

It will be apparent from the earlier discussion of the amphiphilic molecules and of the coupling reagents that a wide range of sensitizer precursors may be synthesized. Further examples include the 2,4-dinitro-5-halo-phenylated derivatives of sphingosin and dihydrophingosin.

Examples of antigenic materials which are to be coupled to the amphiphilic molecules to form sensitizers include vitamins, proteins, peptides, hormones including sex hormones, narcotics, and addictive drugs, as well as pharmaceuticals.

These can be reacted directly or indirectly with an amphiphilic molecule or with a sensitizer precursor to obtain a sensitizer compound. For example, an antigen molecule containing a nucleophilic group may be reacted with the 2,4-dinitro-5-halo-phenylated derivative of a phosphatidylethanolamine, to obtain sensitizer compounds e.g. of the formula:

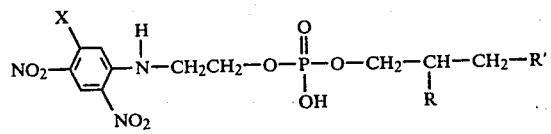

wherein X an antigenic group linked through a divalent polar residue of the nucleophilic group to the benzene ring and R and R' are as defined above.

As representative examples may be mentioned sensitizers wherein the antigenic material residue is identified as follows:

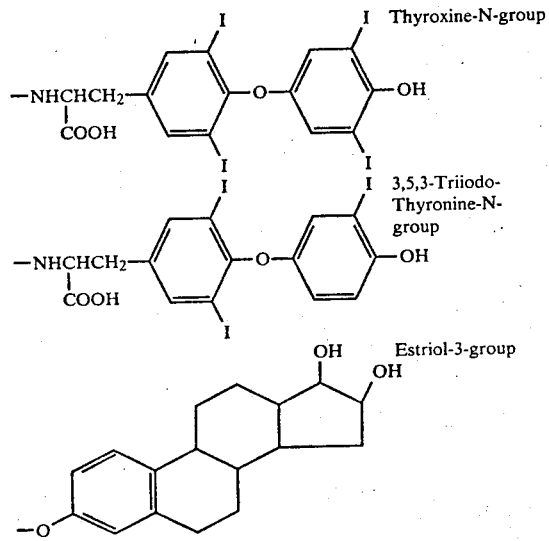

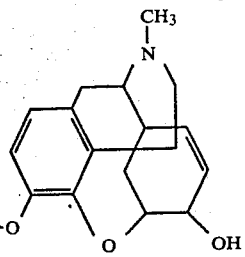 Morphine-3-group

Utilizing the amphiphilic molecules and sensitizer precursors, various sensitizer compounds can be synthesized. These sensitizer compounds have an antigenic material head and a lipid tail portion, and can be incorporated into the lipid bilayer membranes of liposomes using known techniques. One method for producing liposomes containing sensitizers is described by Kinsky et al in the article in Biochemistry referred to previously. This technique may be employed in the preparation of liposomes incorporating antigenic material sensitizers such as have been described above in detail.

In the preparation of the liposomes, as aqueous solution of a detectable marker material is employed which may be for example glucose, or substances such as enzymes, and fluorogenic substrates, although spin label markers are preferred.

In the preparation of the liposomes these aqueous marker solutions become entrapped within concentric shells of lipid bilayers, so that in the structure of the liposome there are concentric shells of lipid bilayer which are separated by aqueous interspaces containing the trapped aqueous marker solution.

The sensitizer whose molecule is constituted by an antigenic material residue linked to a lipid residue, becomes dissolved in the lipid bilayer and is considered to have its molecule orientated generally radially of the liposome structure, with at least some of the sensitizer molecules having the antigenic material head adjacent the external aqueous phase and thus being available for binding with an appropriate antibody.

In the presence of an antibody specific for the hapten in question and in the presence of a source of complement, the sensitized liposome is subjected to lysis and trapped marker is released to an extent dependent on the concentrations of the antibody and of the complement.

The preferred markers are spin label markers such as tempcholine halide

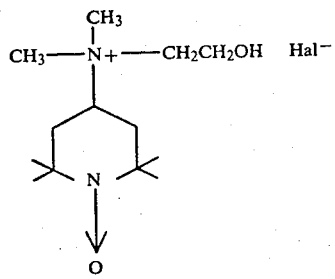

and Fremy's salt $(KO_3S)_2N\rightarrow O$.

The extent of release of these markers can readily be detected using ESR determination. The trapped solution, in which the marker concentration is high, exhibits only broadened and weak ESR spectra, but at low concentrations such as result when the marker is released from the liposome into the external aqueous phase, sharp and distinct ESR peaks are observed, the magnitude of the peak then increasing with increasing concentrations within the range of low concentrations which are encountered under practical conditions.

The use of spin label markers and of ESR techniques for determining the extent of lysis is described in the literature, and is especially convenient. Methods for determining release of other types of marker are also described in the literature.

In making use of these techniques for the purposes of the present invention, a sensitizer corresponding to an antigenic material of interest is synthesized, and a corresponding sensitized liposome is then produced. A specimen of the antigenic material of unknown concentration is then reacted with a standard solution of an antibody specific for the antigenic material, and the solution thus obtained, in which the antibody strength is depleted or inhibited, is then reacted with a standard aqueous liposome suspension in the presence of a standard quantity of complement. Under these conditions, the amount of marker released is related, in a predetermined and fixed relationship, with the quantity of antigenic material present in the specimen to be assayed. Experiments using standard solutions of antigenic material have shown that the extent of marker release from a given quantity of liposomes under these conditions is dependent on the concentrations of complement, antibody, and of antigenic material in the original solution. If the complement and antibody concentrations are maintained constant at known levels, the extent of release of marker can therefore indicate directly the antigenic material content in the unknown solution.

This assay method is also applicable to the simultaneous assay of two or more antigenic materials. In such procedures, two or more different species of liposome are employed, each sensitized with a different antigenic sensitizer, and each containing a different and distinguishable marker solution. For example, where two antigenic materials are to be determined, one species of liposome may contain tempocholine chloride solution and the other may contain a solution of Fremy's salt. These markers have separate and distinct ESR spectra and therefore the release of each marker can be determined independently of the other. In the assay, the solution containing two antigenic materials in unknown concentration are reacted with an antiserum containing standard concentrations of antibodies for both. The resulting solution can then be subjected to the assay procedure as described in more detail above, the respective ESR spectra or other respective indications of marker release then serving to indicate the original concentrations of each unknown antigenic material.

Some Examples illustrative of the invention will now be given.

EXAMPLE 1

Preparation of a sensitizer precursor 1-fluoro-5-N-(phosphotidylethanolamine)-2,4-dinitrobenzene (F-DNP-PE)

In the preparation of this sensitizer precursor, dipalmitoyl-phosphatidylethanolamine (120 mg, 0.173 mmole) was dissolved in 50 ml of chloroform containing 0.1 M of triethylamine. 1,5-difluoro-2,4-dinitrobenzene (194 mg, 0.95 mmole) dissolved in 10 ml of chloroform was then added and the mixture was allowed to stir in the dark at room temperature for 15 hr. The resulting yellow solution was first concentrated under vacuum to about 1 ml and then the product was isolated by preparative thin layer chromatography eluted with methanol and chloroform (1:4).

Yellow band with $R_f=0.70$ was collected yielding yellow solid (125 mg, ~80%) which had the following physical properties: mp, 75°-77°; IR (CHCHl$_3$): $\gamma_{max}$ 3650, 2940, 2850, 1730, 1630, and 1605 cm$^{-1}$; UV (MeOH): $\lambda_{max}$ 222, 262, 338, and 390 (shoulder) nm.

EXAMPLE 2

Preparation of an analogue to a sensitizer precursor 3-dinitrophenyl-0-5α-cholestane 100 Mg of 5-α-cholestane-3β-ol and a small stirring bar were dried for 69 min at 100° C. in a vial. The vial was sealed with a rubber septum and 5 ml of dry tetrahydrofuran (THF) distilled from LiALH$_4$, was added via a syringe. With rapid stirring 0.35 ml of potassium tert-butoxide was added (80 mgK/ml) was added slowly over 15 minutes. There is a tendency for a precipitate to form which can be overcome by adding more dry THF. The solution formed a pale yellow colour indicative of anion formation. After stirring for approximately 30 min., 0.5 ml of 1-fluoro-2,4-dinitrobenzene solution, (130 mg/ml of THF), was added via a syringe.

A yellow ppt. formed and the reaction mixture was allowed to stand overnight. The reaction mixture was then evaporated to dryness and taken up in 10 ml of chloroform and filtered. The filtrate was chromatographed on 1 mm silica gel plates with chloroform: hexane (60:40 v/v) as the developing solvent. The front running band was collected yielding a white solid. Recrystallyzed from methanol: chloroform the melting point was 196°-197° C., yield=0.024 g. The IR indicated no OH absorption. Bands were found at 2940 CH, 2860 CH, 1615 DNP, 1530 NO$_2$, 1350 NO$_2$. The calculated molecular weight is 555. Mass spectrum analysis: parent peek 555 $\rho_{302}$=11,900 M$^{-1}$cm$^{-1}$.

EXAMPLE 3

Preparation of an analogue to a sensitizer precursor

N,N'-bis(dinitrophenyl)-lysyl-phosphatidylethanolamine

The subject compound was synthesized by direct coupling of N,N'bis(dinitrophenyl)-L-lysine to dipalmitolyl phosphatidylethanolamine using N,N'-carbonyldiimadazole. ($\geq$4 mg, 0.0015 mmole) and bis-DNP-lysine (6.9 mg, 0.014 mmole) dissolved in dimethylformamide (Pierce Chemical Co.) were stirred for 2 hr. at 50°. The solution was then added to a solution of the phosphatidylethanolamine (10 mg dissolved in 2 ml DMF). The reaction mixture was allowed to react at 50° for 3 days. The pure product (~40% yield), isolated by preparative thin layer chromatography with 20% MeOH in CHCl$_3$ as the solvent, has the following physical properties: yellow solid; UV=$\lambda_{max}^{MeOH}$, 220, 350, and 415 nm; IR: U$_{max}$ (CHCl$_3$): 3370, 2940, 2850, 1730, 1670, 1620 and 1340 cm$^{-1}$; $R_f$=0.56.

EXAMPLE 4

Preparation of a sensitizer precursor 4-fluoro-3,3'-dinitrophenyl sulfone - PE

Dipalmitoyl phosphatidylethanolamine (200 mg, 0.29 mmole Supreme Chem. Co.) and triethylamine (10 drops) were dissolved in 30 ml. of chloroform and then added to a solution containing 4,4'-di-fluoro-3,3'-dinitrophenyl sulfone (Pierce Chemical Company, 200 mg, 0.60 mmole) in 20 ml of chloroform. The mixture was stirred at room temperature overnight. Thin-layer chromatography (methanol-chloroform, 1:7, silica gel plates from Eastman Kodak Company, Rochester, N.Y.) showed no remaining PE (ninhydrin test). The reaction mixture was concentrated to about 5 ml. The desired yellow product was isolated by preparative thin-layer chromatography using methanol-chloroform (1:9) as solvent. $R_f$ value for the product was 0.6. The yield was 216 mg (73.6%). The pure product was obtained by second preparative thin-layer chromatography and had the following physical properties. IR(CHCl$_3$):$\gamma_{max}$ 3690, 3380, 2940, 2860, 1740, 1620, 1540, 1470, 1345, 1340, cm$^{-1}$ UV(CHCl$_3$) $\lambda_{max}$ 280 (Sh), 290 and 410 nm.

EXAMPLE 5

Preparation of a sensitizer

Thyroxine-DNP-PE (2,4-dinitro-5-(thyroxine-N-)phenylated dipalmitoyl phosphatidylethanolamine)

60 mg of thyroxine (obtained from Sigma Chemical Company St. Louis, Miss.) in the form of the sodium salt pentahydrate (10.067 mmole) and 6 mg NaHCO$_3$ were dissolved in 20 ml of methanol. 60 mg (0.036 mmole) of F-DNP-PE as obtained in Example 1 dissolved in 5 ml chloroform was added slowly to the thyroxine. The mixture was stirred at 50° C. for 24 hours. The solvent was removed under reduced pressure. The residue was dissolved in a small amount of chloroform and was purified by preparative thin layer chromatography on a silica gel plate eluted with methanol and chloroform (1:4) as solvents. The yellow solid from a yellow band ($R_f$=0.4) was rechromatographed on a silica gel plate (1 mm) with methanol and chloroform to give a pure solid (64.6 mg, 58%) which has the following physical properties: mp: IR(CHCl$_3$): $\gamma_{max}$ 3650, 3200, 3930, 2850, 1730, 1610, 1590, 1405, and 1100 cm$^{-1}$; UV.(CHCl$_3$): $\lambda_{max}$ 246 (24,500), 335 (24,700) and 412 (8,900) nm.

EXAMPLE 6

Preparation of a sensitizer 3,5,3'-triiodothyronine-DNP-PE

Following the procedure of Example 4 and using the equivalent quantity of 3,5,3'-triiodothyronine in place of thyroxine, 3,5,3'-triiodothyronine-DNP-PE is obtained.

EXAMPLE 7

Preparation of a sensitizer

Estriol-3-DNP-PE

To a solution of estriol in methanol a mixture of sodium hydroxide and methanol in 1:1 mol ratio is added, in an amount sufficient to provide the stoichiometric amount of sodium required to obtain the sodium salt of the estriol as estriol-3-phenoxide anion.

To the solution which is obtained, there is added a solution in methanol of F-DNP-PE as obtained in Example 6. The resulting solution may be heated at 50° C. with stirring for 30 mins. or may be stirred at room temperature overnight. The above-captioned product is obtained in solution.

EXAMPLE 8

Preparation of a sensitizer

Morphine-3-DNP-PE

The procedure of Example 6 is followed using morphine in place of estriol. Morphine-3-0- sodium salt is obtained as an intermediate and is converted to the captioned product.

EXAMPLE 9

Preparation of a sensitizer

Preparation of Thyroxine-DNDPS-PE

Thyroxine in the form of sodium salt (Sigma Chem. Co. 52 mg, 0058 mmole) and sodium bicarbonate (5 mg) was dissolved in 20 ml of methanol. F-DNDPS-PE (60 mg, 0060 mmole) obtained as in Example 4, dissolved in 2 ml of chloroform was added to the T4 solution. The reaction mixture was allowed to stir at 50° C. for 24 hr. The solvent was then removed under reduced pressure on a rotating vacuum evaporator. The dried material was redissolved in chloroform and purified by preparative thin-layer chromatography using silica gel as an absorbent methanol-chloroform (25:75) as the developer. The yellow spot has $R_f$ of about 0.25 which was not overlapped with the starting materials. The product was isolated yielding 72 mg of thyroxine-DNDPS-PE (66%). An analytical sample was obtained by several preparative thin-layer chromatography which had the following physical properties: UV(CHCl$_3$) $\lambda_{max}$ 250 (40,600); 265 (sh); 295 (30,000); and 410 (7,500) nm.

EXAMPLE 10

Preparation of thyroxine-antiserum sensitive liposomes

The procedure followed was generally the same as that described by Kinsky et al.

Lipids consisting of sphingomyelin, cholesterol, dicetyl phosphate and thyroxine-DNP-PE, as obtained in Example 4, in the molar ratio of 2:1.5:0.22:0.05 were placed in a small test-tube (12×75 mm). The resulting lipid mixture and methanol was dried using a rotary evaporator under reduced pressure and further with vacuum in the dessicator for at least one hour. The dried lipids coated on the inner surface of the glass of the test-tube were swollen in an isotonic buffer solution which contained 0.1 M tempocholine chloride (spin label marker). The lipids were then dispersed with the help of two small glass beads and brief vortexing. The resulting milky liposome suspension was dialyzed against at least three changes of 1000 volumes of 0.15 M NaCl solution to remove the untrapped marker.

EXAMPLE 11

Examples of assay procedure.

All ESR determinations were performed on a Varian (Varian Co., Palo Alto, California) E-6 spectrometer utilizing uniform glass capillary tubes holding a constant volume of approximately 25 μl (Yankee, disposable micropipette). The method for measuring spin label release caused by immune damage to liposome was essentially identical to the previously described methods by E. G. Humphries and H. M. McConnell (Proc. Nat. Acad. Sci. U.S.A., 71, No. 5, pp 1691-4).

The dialyzed liposome suspension from Example 8 incorporating a specific sensitizer was diluted a hundred times with 0.15 M NaCl solution containing 1 MM MgCl$_2$ and 0.15 M NaCl solution containing 1 mM MgCl₂ and 0.15 mM CaCl₂. In a total volume of 100 μl, 20 μl of the diluted liposomes were incubated with quantities of aqueous thyroxine antiserum and quantities of standard aqueous thyroxine solution. The immune reaction was started by adding an amount of fresh guinea pig serum determined as a complement source. The degree of lysis was determined by the high field peak height in the ESR spectrum, indicating the amount of spin label marker released from the liposomes.

It is found that the degree of lysis is dependent on the concentration of complement, of thyroxine, and of thyroxine antiserum.

Using known standard thyroxine solutions, and at predetermined concentrations of complement and antiserum a standard curve relating the degree of lysis to the concentration of thyroxine is obtained.

From the standard curve, the concentration of thyroxine in an unknown specimen can be determined by subjecting the specimen to assay under standardized conditions.

It is found that the assay procedure is specific and is highly sensitive, capable of detecting quantities of antigenic material in the range $10^{-7}$ to $10^{-12}$ mole.

As compared with radio immunoassay, the assay described above in detail represents a considerable reduction in the cost of the assay method, and it uses reagents which are relatively cheap and are not subject to errors and hazards resulting from radio active decay. Further, it does not require separation procedures and thus reduces the risk of human error.

We claim:

1. A synthetic sensitizer for use in forming sensitized liposomes and characterized by a molecular structure comprising an antigenic radical selected from the group consisting of thyroxine-N-group, and 3,5,3'-triiodothyronine-N-group linking to the 5-position of a 2,4-dinitro-phenylene group and said phenylene group being linked at the 1-position to an amphiphilic radical selected from the group consisting of phosphatidyl esters of hydroxyamines, amino-acylated phosphatidyl esters of hydroxy amines, cholesterols, sphingosins and dihydrosphingosins.

2. A sensitizer as claimed in claim 1 wherein said amphiphilic radical is selected from the group consisting of phosphatidylethanolamines, aminocarboxyl phosphatidylethanolamines, and N,N'-bis (dinitro-halo-phenyl)-diaminocarboxyl phosphatidylethanolamine.

3. A sensitizer as claimed in claim 1 wherein said amphiphilic radical is selected from the group consisting of (a) phosphatidylethanolamines of the formula

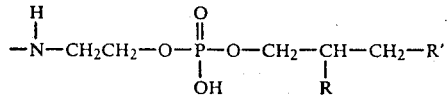

wherein R and R' are independently H, OH, R" or

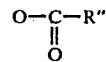

wherein R" is a saturated or unsaturated branched or straight chain alkyl or alkylene group of 1 to 24 carbons, and wherein at least one of R and R' is

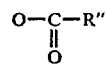

or OR";

(b) aminocapropyl phosphatidylethanolamines of the formula

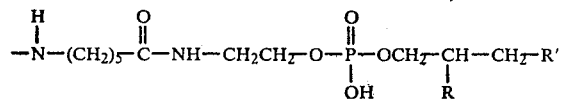

wherein R and R' are as defined above; and (c) divalent lysyl phosphatidylethanolamine of the formula

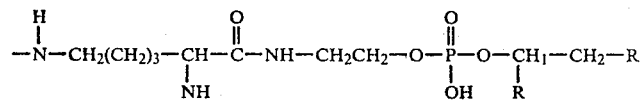

wherein R and R' are as defined above and each NH— group is linked through a 2,4-dinitrophenylene group to said antigen.

4. A sensitizer comprising the compound 2,4-dinitro-5-(thyroxine-N-) phenylated dipalmitoyl phosphatidylethanolamine.

5. A sensitizer characterized by a molecular structure consisting of an antigen group selected from the group consisting of thyroxine-N-group and 3,5,3'-triiodothyronine-N-group linked to the 4-position of 3,3'-dinitrophenylene sulfone residue of which the 4' position is linked to an amphiphilic group selected from the group consisting of (a) phosphatidylethanolamines of formula

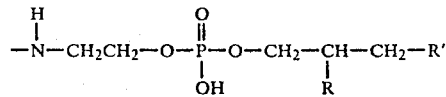

wherein R and R' are independently H, OH, R" OR" or

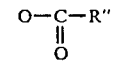

wherein R" is a saturated or unsaturated, branched or straight chain alkyl or alkylene group of 1 to 24 carbons, and wherein at least one of R and R' is

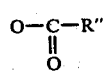
or OR'';
(b) aminocaproyl phosphatidylethanolamines of formula
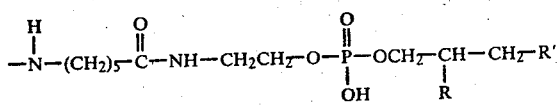
wherein R and R' are as defined above;
and (c) divalent lysyl phosphatidylethanolamine of formula
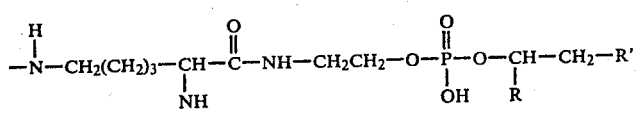
wherein R and R' are as defined above and each NH— group is linked through the 4- and 4'- position of a 3,3'-dinitrophenylene sulfone residue to said antigen group.
* * * * *